US012752263B2

(12) United States Patent
Pengpanich et al.

(10) Patent No.: US 12,752,263 B2
(45) Date of Patent: Oct. 6, 2026

(54) CATALYST FOR LIGHT OLEFINS PRODUCTION AND A PROCESS OF LIGHT OLEFINS PRODUCTION BY USING A CATALYST THEREOF

(71) Applicant: PTT GLOBAL CHEMICAL PUBLIC COMPANY LIMITED, Chatuchak (TH)

(72) Inventors: Sitthiphong Pengpanich, Chatuchak (TH); Kaew-arpha Thavornprasert, Chatuchak (TH); Apipornchai Singtee, Chatuchak (TH)

(73) Assignee: PTT Global Chemical Public Company Limited, Chatuchak (TH)

( * ) Notice: Subject to any disclaimer, the term of this patent is extended or adjusted under 35 U.S.C. 154(b) by 0 days.

(21) Appl. No.: 18/029,007

(22) PCT Filed: Jan. 10, 2023

(86) PCT No.: PCT/IB2023/050189
§ 371 (c)(1),
(2) Date: Mar. 28, 2023

(87) PCT Pub. No.: WO2023/194809
PCT Pub. Date: Oct. 12, 2023

(65) Prior Publication Data

US 2025/0018381 A1 Jan. 16, 2025

(30) Foreign Application Priority Data

Apr. 7, 2022 (TH) ................................ 2201002112

(51) Int. Cl.
*B01J 29/035* (2006.01)
*B01J 29/40* (2006.01)
(Continued)

(52) U.S. Cl.
CPC ............... *B01J 29/69* (2013.01); *B01J 29/48* (2013.01); *B01J 35/19* (2024.01); *B01J 35/398* (2024.01);
(Continued)

(58) Field of Classification Search
CPC . B01J 29/035; B01J 29/40; B01J 29/48; B01J 29/65; B01J 29/69; B01J 29/80;
(Continued)

(56) References Cited

U.S. PATENT DOCUMENTS 3,263,320 A 8/1966 Jones
6,222,087 B1 4/2001 Johnson et al.
(Continued)

FOREIGN PATENT DOCUMENTS

CN 107670687 A 2/2018
CN 108946764 A 12/2018
(Continued)

OTHER PUBLICATIONS

Wuamprakhon et al., "Direct synthesis of hierarchical ferrierite nanosheet assemblies via an organosilane template approach and determination of their catalytic activity." Microporous and Mesoporous Materials, vol. 219, pp. 1-9 (2016).
(Continued)

*Primary Examiner* — Cam N. Nguyen
(74) *Attorney, Agent, or Firm* — Troutman Pepper Locke LLP

(57) ABSTRACT

The present invention relates to a catalyst for light olefins production from catalytic cracking of hydrocarbon having 4 to 7 carbon atoms, wherein said catalyst has core-shell structure comprising zeolite core selected from ferrierite, ZSM-5, or mixture thereof, and silicalite shell having MFI structure, and said catalyst has the following characteristics: a) the weight ratio of shell to core greater than 0 but less than
(Continued)

4; b) the mole ratio of silica to alumina ($SiO_2/Al_2O_3$) from 60 to 550; c) the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.35 to 0.90, and said mesopores comprise pores having pore size from 2 to 5 nm, wherein the proportion of volume of pores having pore size from 2 to 5 nm to the total pore volume is in the range from 0.08 to 0.30. The catalyst according to the invention provides high conversion of the reactant and especially high selectivity to light olefins. Moreover, this invention also relates to the process of light olefins production by using the catalyst thereof.

37 Claims, 6 Drawing Sheets

(51) Int. Cl.

| | |
|---|---|
| ***B01J 29/46*** | (2006.01) |
| ***B01J 29/48*** | (2006.01) |
| ***B01J 29/65*** | (2006.01) |
| ***B01J 29/69*** | (2006.01) |
| ***B01J 29/80*** | (2006.01) |
| ***B01J 35/00*** | (2006.01) |
| ***B01J 35/30*** | (2024.01) |
| ***B01J 35/40*** | (2024.01) |
| ***B01J 35/45*** | (2024.01) |
| ***B01J 35/53*** | (2024.01) |
| ***B01J 35/60*** | (2024.01) |
| ***B01J 35/63*** | (2024.01) |
| ***B01J 35/64*** | (2024.01) |
| ***B01J 35/70*** | (2024.01) |
| ***B01J 35/80*** | (2024.01) |
| ***C07C 4/06*** | (2006.01) |
| ***C07C 11/04*** | (2006.01) |
| ***C07C 11/06*** | (2006.01) |
| ***C10G 11/05*** | (2006.01) |

(52) U.S. Cl.

CPC ........... *B01J 35/633* (2024.01); *B01J 35/635* (2024.01); *B01J 35/647* (2024.01); *C07C 4/06* (2013.01); *B01J 35/70* (2024.01); *B01J 2229/62* (2013.01); *B01J 2235/30* (2024.01); *C07C 2529/48* (2013.01); *C07C 2529/69* (2013.01)

(58) Field of Classification Search

CPC ... B01J 35/19; B01J 35/60; B01J 35/70; B01J 35/398; B01J 35/633; B01J 35/635; B01J 35/647; B01J 2235/30; B01J 2229/62; B01J 29/405; B01J 29/46; B01J 35/45; B01J 35/53; C07C 2529/48; C07C 2529/69; C07C 11/04; C07C 11/06; C07C 4/06; C10G 11/05

USPC ............................................................ 502/66

See application file for complete search history.

(56) References Cited

U.S. PATENT DOCUMENTS

| | | | | |
|---|---|---|---|---|
| 6,858,129 | B2 | 2/2005 | Mohr et al. | |
| 7,981,273 | B2 | 7/2011 | Nicholas et al. | |
| 8,157,985 | B2 | 4/2012 | Nicholas et al. | |
| 9,884,794 | B2 * | 2/2018 | Al-Khattaf | B01J 37/0201 |
| 10,159,967 | B1 | 12/2018 | Al-Khattaf et al. | |
| 10,159,968 | B1 * | 12/2018 | Al-Khattaf | B01J 37/0244 |
| 11,192,094 | B2 * | 12/2021 | Rownaghi | B01J 29/084 |
| 11,801,499 | B2 * | 10/2023 | Wattanakit | B01J 35/19 |
| 2002/0183192 | A1 | 12/2002 | Verduijm et al. | |
| 2006/0011514 | A1 | 1/2006 | van den Berge et al. | |
| 2010/0105974 | A1 | 4/2010 | Towler et al. | |
| 2015/0018590 | A1 * | 1/2015 | Stevenson | C07C 2/12 423/713 |
| 2018/0193826 | A1 | 7/2018 | Al-Khattaf et al. | |
| 2021/0322961 | A1 | 10/2021 | Wattanakit et al. | |
| 2023/0038518 | A1 * | 2/2023 | Wattanakit | B01J 35/651 |
| 2024/0226860 | A1 * | 7/2024 | Jan | C10G 3/49 |

FOREIGN PATENT DOCUMENTS

| | | | | |
|---|---|---|---|---|
| CN | 110882718 | A | 3/2020 | |
| CN | 109569701 | B | 8/2021 | |
| CN | 113751057 | A | 12/2021 | |
| CN | 113908879 | A | 1/2022 | |
| EP | 0550270 | B1 | 9/1996 | |
| MY | 120519 | A | 11/2005 | |
| WO | 1996016004 | A2 | 5/1996 | |
| WO | 1997045198 | A1 | 4/1997 | |
| WO | WO-2018011652 | A1 * | 1/2018 | B01J 29/80 |
| WO | 2018157042 | A1 | 8/2018 | |
| WO | WO-2021130686 | A1 * | 7/2021 | C07C 11/08 |

OTHER PUBLICATIONS

Suttipat et al., "Fine-tuning the surface acidity of hierarchical zeolite composites for methanol-to-olefins (MTO) reaction. Fuel." vol. 286, Part 1, (2021).

International Search Report and Written Opinion issued in International Application No. PCT/IB2023/050189 dated Jun. 6, 2023.

* cited by examiner

CATALYST FOR LIGHT OLEFINS PRODUCTION AND A PROCESS OF LIGHT OLEFINS PRODUCTION BY USING A CATALYST THEREOF

This application is a U.S. national stage application of International Application No. PCT/IB2023/050189, filed on Jan. 10, 2023, which claims priority to Thai patent application Ser. No. 2201002112, filed Apr. 7, 2022. The entire contents of which is hereby incorporated by reference in their entirety.

TECHNICAL FIELD

The present invention relates to the field of chemistry, in particular, to a catalyst for light olefins production from catalytic cracking of hydrocarbon having 4 to 7 carbon atoms, and a process of light olefins production by using a catalyst thereof.

BACKGROUND OF THE INVENTION

The light olefins, which are ethylene and propylene, are the important reactants in the production of polymers, especially polyethylene and polypropylene. Generally, the light olefins are produced industrially by the thermal steam cracking process from the reactants, which are naphtha or ethane separated from natural gas. However, it is found that the production of the light olefins by said process has disadvantage in term of energy consumption because it needs high heat at temperature of 800 to 900° C. It also has problem of the accumulation of lots of heavy hydrocarbons having more than 9 carbon atoms in the system or the so-called coking. This causes the production process to be stopped frequently for the maintenance of the reactor. Therefore, there is the alternative process which is the production process of the light olefins from catalytic cracking of naphtha. This has advantage in the ability to produce large numbers of light olefins using lower reaction temperature, then reducing the energy consumption in the production and reducing the coking problem in the system.

Zeolite is the crystalline aluminosilicate compound having outstanding properties such as adjustable acidity-basicity according to the reaction employed, thermal and chemical stability, and shape selectivity. Therefore, zeolite has been applied to various works such as adsorbent, ion exchanger, and heterogeneous catalysts that can act as catalyst or support. The process of light olefins production from catalytic cracking using zeolite as the catalyst is interesting and popular because zeolite contains suitable catalytic acid site and also has porosity having specific properties for the selectivity of the preferred products.

The documents which have disclosed or reported about the process of light olefins production from catalytic cracking of naphtha using zeolite as the catalyst are as follows.

Patent documents U.S. Pat. Nos. 7,981,273B2, 8,157,985B2, and US20100105974A1 disclose the aluminosilicate or zeolite catalyst for the process of olefins production from catalytic cracking of hydrocarbon including naphtha by adding potassium, sodium, gallium, and organoammonium cation compounds. It also included the development of the catalyst which was the mixture of different types of zeolites between small pore zeolite such as chabazite, erionite, ferrierite, and ZSM-22, and intermediate pore zeolite which was nano-silicalite having the silica to alumina ratio greater than 200, preferably the silica to alumina ratio in the range between 600 to 1600.

Patent document U.S. Pat. No. 6,222,087B1 and US326332B2 disclose the catalyst for the process of olefins production from catalytic cracking of hydrocarbon including naphtha and hydrocarbon having 4 to 7 carbon atoms using the catalyst comprising various zeolites which were ZSM-5, ZSM-11, or mixture thereof, wherein said zeolites had the silica to alumina ratio greater than 300; and phosphorous addition. It also included the development of the catalyst which was the mixture of different types of zeolites between a first zeolite having intermediate pore size, a second zeolite having different structure from the first zeolite and having pore size index less than pore size index of the first zeolite, and optionally a third zeolite.

Patent document CN107670687A discloses the composition of the zeolite catalyst having core-shell structure and the preparation process of said catalyst. The core was nano ZSM-5 and the shell was silicalite-1 prepared from the use of tetrapropylammonium hydroxide (TPAOH) as the structure-directing agent of the zeolite.

Patent document WO1997045198A1 discloses the composition of the zeolite bound zeolite catalyst comprising a first zeolite and a binder comprising a second zeolite having different structure from the first zeolite. The second zeolite might partially coat on the first zeolite. Both zeolites might have the small pore size in the range of 3 to 5 Å, the intermediate pore size in the range of 5 to 7 Å, or the large pore size greater than 7 Å.

Patent document CN113751057A discloses the preparation process of ZSM-5 zeolite catalyst coated by silica or silicalite-1. Said document discloses the preparation process of silica or silicalite shell coated on ZSM-5 by impregnation method. Patent document CN113908879A also discloses the preparation process of ZSM-5 zeolite catalyst coated by silicalite-1.

Patent document WO1996016004A2 discloses the composition of the zeolite bound zeolite catalyst comprising a first zeolite and a binder comprising a second zeolite having average particle size less than the first zeolite. Both zeolites might be selected from medium pore zeolite in the range of 5 to less than 7 Å, large pore zeolite greater than 7 Å, or mixture thereof.

Patent document US20060011514A1 discloses the composition of the zeolite catalyst comprising a first zeolite and a layer of a second zeolite having average particle size less than the first zeolite and covering at least a portion of surface of the first zeolite. Both zeolites might have small pore size in the range of 3 to 5 Å, the intermediate pore size in the range of 5 to 7 Å, or the large pore size greater than 7 Å.

Patent document MY120519A discloses the composition of the zeolite bound zeolite catalyst comprising a first zeolite and a binder comprising a second zeolite having different structure from the first zeolite, and an non-zeolitic binder in the amount less than 10%. Both zeolites might have small pore size in the range of 3 to 5 Å, the intermediate pore size in the range of 5 to 7 Å, or the large pore size greater than 7 Å.

Patent document U.S. Pat. No. 6,858,129B2 discloses the process for converting hydrocarbon using zeolite bound zeolite catalyst comprising core comprising a first zeolite and optionally a second zeolite, and binder comprising a third zeolite and optionally a fourth zeolite, wherein at least one of the second zeolite, the fourth zeolite, or both zeolites were present in an amount of 1 to 70% by weight of the catalyst. Said zeolites might be selected from small pore zeolite in the range of 3 to 5 Å, intermediate pore zeolite in the range of 5 to 7 Å, or large pore zeolite greater than 7 Å.

Patent document US20180193826A1 and U.S. Ser. No. 10/159,967B1 discloses the core-shell catalyst comprising ZSM-5 zeolite as the core and the silica shell having a thickness in the range of 0.5 to 50 m and the preparation process of said catalyst using quaternary ammonium salt as the structure-directing agents of the zeolite. From the preparation process disclosed in said document, the obtained catalyst was the conventional zeolite having a majority of the portion of small pore size.

Nevertheless, it has been found that the use of the conventional zeolite as the catalyst has limitations such as low catalytic activity, quick deterioration, and difficulty and complexity in the regeneration process of the catalyst. This is because the conventional zeolite has mass transfer and diffusion limit which results from pore size of the zeolite structure having very small size in angstrom unit in the structure of large zeolite crystal, causing the critical mass transfer and then leading to difficulty for the reactant molecules to access to the active sites. Moreover, the intermediates may occur the recombination to form the coking, leading to the catalyst deterioration. When using the conventional zeolite as the catalyst in the process of light olefins production from catalytic cracking of hydrocarbon, it is found that there is still the limitation of the selectivity to light olefins because of the product formation from side reactions at the active sites on the external surface.

From these reasons, the development of the zeolite catalyst having hierarchical pores is important because it is highly specific in the production of light olefins from naphtha via the catalytic cracking. When considering all documents above, it is found that there is no disclosure on the core-shell zeolite catalyst having hierarchical pores comprising mesopores and macropores in the range from 2 nm or more, wherein the proportions of mesopores and macropores are greater than the conventional zeolite and the proportions of different pores are suitable for the process of light olefins production from catalytic cracking. Moreover, some documents have not disclosed the suitable ratio of core and shell in the catalyst having core-shell structure. These are factors that affect the efficacy of the catalyst in the process of light olefins production.

From above reasons, this invention aims to prepare the catalyst for light olefins production from catalytic cracking of hydrocarbon having 4 to 7 carbon atoms and process of light olefins production by using the catalyst thereof, wherein said catalyst is suitable to be used in the process of light olefins production, provides high conversion of the reactant, and especially high selectivity to light olefins.

SUMMARY OF THE INVENTION

The present invention aims to prepare the catalyst for light olefins production from catalytic cracking of hydrocarbon having 4 to 7 carbon atoms, wherein said catalyst has core-shell structure comprising zeolite core selected from ferrierite, ZSM-5, or mixture thereof, and silicalite shell having MFI structure, and said catalyst has the following characteristics:

a) the weight ratio of shell to core greater than 0 but less than 4;

b) the mole ratio of silica to alumina ($SiO_2/Al_2O_3$) from 60 to 550;

c) the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.35 to 0.90, and said mesopores comprise pores having pore size from 2 to 5 nm, wherein the proportion of volume of pores having pore size from 2 to 5 nm to the total pore volume is in the range from 0.08 to 0.30.

In another embodiment, this invention relates to the process of light olefins production from catalytic cracking of hydrocarbon having 4 to 7 carbon atoms, comprising the contact of the hydrocarbon having 4 to 7 carbon atoms to the catalyst at the temperature in the range from 400 to 700° C. and the pressure in the range from 0.1 to 10 bars, wherein said catalyst has core-shell structure comprising zeolite core selected from ferrierite, ZSM-5, or mixture thereof, and silicalite shell having MFI structure, and said catalyst has the following characteristics:

a) the weight ratio of shell to core greater than 0 but less than 4;

b) the mole ratio of silica to alumina ($SiO_2/Al_2O_3$) from 60 to 550;

c) the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.35 to 0.90, and said mesopores comprise pores having pore size from 2 to 5 nm, wherein the proportion of volume of pores having pore size from 2 to 5 nm to the total pore volume is in the range from 0.08 to 0.30.

DETAILED DESCRIPTION

Figure 1:
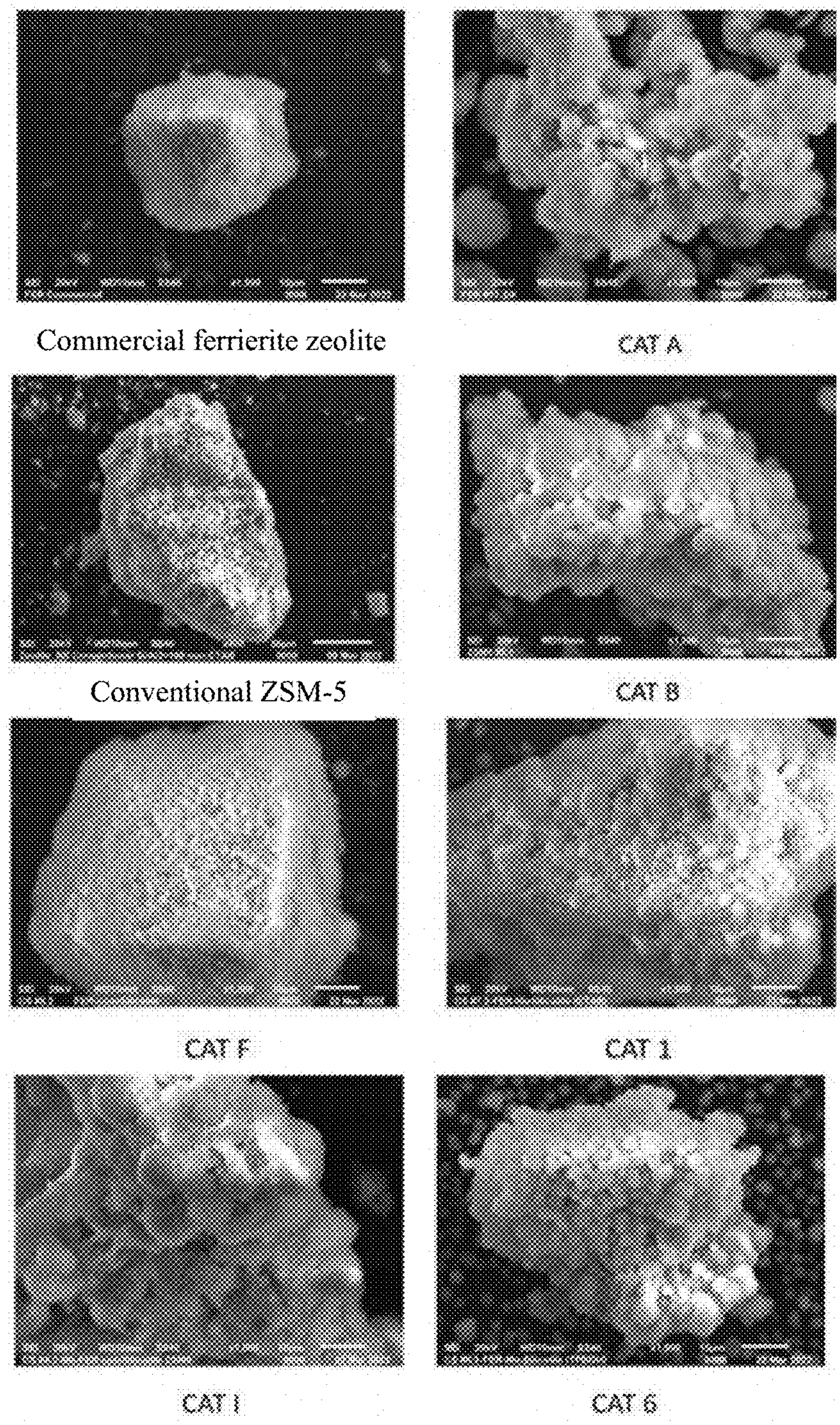
FIG. 1 shows the characteristics of the crystalline structure tested by scanning electron microscope (SEM) technique.

The present invention relates to the catalyst for the light olefins production from catalytic cracking of hydrocarbon having 4 to 7 carbon atoms and process of light olefins production by using the catalyst thereof, wherein said catalyst is suitable to be used in the process of light olefins production, provides high conversion of the reactant, and especially high selectivity to light olefins, which will be described in the following aspects of the invention.

Any aspect being described herein also means to include the application to other aspects of this invention unless stated otherwise.

Technical terms or scientific terms used herein have definitions as understood by an ordinary person skilled in the art unless stated otherwise.

Any tools, equipment, methods, or chemicals named herein mean tools, equipment, methods, or chemicals being operated or used commonly by those person skilled in the art unless stated otherwise that they are tools, equipment, methods, or chemicals specific only in this invention.

Use of singular noun or singular pronoun with "comprising" in claims or specification means "one" and also including "one or more", "at least one", and "one or more than one".

All compositions and/or methods disclosed and claims in this application are intended to cover embodiments from any operation, performance, modification, or adjustment any factors without any experiment that significantly different from this invention and obtain with object with utility and resulted as same as the present embodiment according to person ordinary skilled in the art although without specifically stated in claims. Therefore, substitutable, or similar object to the present embodiment, including any minor modification or adjustment that can be apparent to person skilled in the art should be construed as remains in spirit, scope, and concept of invention as appeared in appended claims.

Throughout this application, term "about" means any number that appeared or expressed herein that could be varied or deviated from any error of equipment, method, or personal using said equipment or method, including variations or deviations occurred from changes in reaction conditions of uncontrollable factors such as humidity and temperature. Zeolite in this invention means the microporous alumino-silicate compound comprising silicon, aluminium, and oxygen in the structure. It may further comprise other elements. Zeolite may be commercial zeolite, natural zeolite, or zeolite prepared by any method.

Silicalite in this invention means the zeolite compound having multi-crystalline structure, wherein the silica to alumina ratio is infinity ($SiO_2/Al_2O_3=\infty$).

Hereafter, invention embodiments are shown without any purpose to limit any scope of the invention.

The present invention relates to the catalyst for light olefins production from catalytic cracking of hydrocarbon having 4 to 7 carbon atoms, wherein said catalyst has core-shell structure comprising zeolite core selected from ferrierite, ZSM-5, or mixture thereof, and silicalite shell having MFI structure, and said catalyst has the following characteristics:

a) the weight ratio of shell to core greater than 0 but less than 4;
b) the mole ratio of silica to alumina ($SiO_2/Al_2O_3$) from 60 to 550;
c) the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.35 to 0.90, and said mesopores comprise pores having pore size from 2 to 5 nm, wherein the proportion of volume of pores having pore size from 2 to 5 nm to the total pore volume is in the range from 0.08 to 0.30.

In one aspect of the invention, said catalyst has the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.40 to 0.90, preferably in the range from 0.40 to 0.70.

In one aspect of the invention, said mesopores comprise pores having pore size from 2 to 5 nm, wherein the proportion of volume of pores having pore size from 2 to 5 nm to the total pore volume is in the range from 0.10 to 0.20.

In one aspect of the invention, said mesopores further comprise pores having pore size from 5 to 8 nm and pores having pore size from 8 to 18 nm.

In one aspect of the invention, said mesopores further comprise pores having pore size from 5 to 8 nm and pores having pore size from 8 to 18 nm, wherein the proportion of volume of pores having pore size from 5 to 8 nm to the total pore volume is in the range from 0.05 to 0.20, preferably in the range from 0.05 to 0.15.

In one aspect of the invention, said mesopores further comprise pores having pore size from 5 to 8 nm and pores having pore size from 8 to 18 nm, wherein the proportion of volume of pores having pore size from 8 to 18 nm to the total pore volume is in the range from 0.05 to 0.30, preferably in the range from 0.05 to 0.20.

In one aspect of the invention, said zeolite core has the hierarchical pores comprising micropores having pore size in the range of 0.1 to 2 nm, mesopores having pore size in the range of 2 to 50 nm, and macropores having pore size greater than 50 nm.

In one aspect of the invention, said zeolite core has the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.30 to 0.90, preferably in the range from 0.30 to 0.80.

In one aspect of the invention, said zeolite core has the hierarchical pores and is arranged in nano-sheet.

In one aspect of the invention, said silicalite shell has the hierarchical pores comprising micropores having pore size in the range of 0.1 to 2 nm, mesopores having pore size in the range of 2 to 50 nm, and macropores having pore size greater than 50 nm.

In one aspect of the invention, said silicalite shell has the hierarchical pores and is arranged in nano-sheet.

In one aspect of the invention, said silicalite shell has the mole ratio of silica to alumina of infinity.

In one aspect of the invention, said zeolite core has the mole ratio of silica to alumina in the range from 35 to 320.

In one aspect of the invention, said zeolite core is the ferrierite having the flower shape-like particle arrangement when analyzed by the scanning electron microscope (SEM) technique at the accelerating voltage of 20 kV with SEI mode.

In one aspect of the invention, said catalyst has the weight ratio of shell to core greater than 0 but less than or equal to 3.

In one aspect of the invention, said catalyst has the mole ratio of silica to alumina in the range from 100 to 400.

In one aspect of the invention, said catalyst has the specific surface area ($S_{BET}$) in the range from about 300 to 800 $m^2/g$, preferably from about 400 to 700 $m^2/g$.

In one aspect of the invention, said catalyst has the external specific surface area ($S_{ext}$) in the range from about 50 to 300 $m^2/g$, preferably from about 70 to 250 $m^2/g$, most preferably from about 80 to 200 $m^2/g$.

In one aspect of the invention, said catalyst comprises the ZSM-5 core having the mole ratio of silica to alumina in the range from 120 but no more than 300 and the silicalite shell, and said catalyst has the weight ratio of shell to core greater than 0 but less than or equal to 1.5.

In one aspect of the invention, said catalyst comprises the ZSM-5 core having the mole ratio of silica to alumina in the range from 50 but no more than 120 and the silicalite shell, and said catalyst has the weight ratio of shell to core greater than 0 but less than or equal to 3.

In one aspect of the invention, said catalyst comprises the ferrierite core having the mole ratio of silica to alumina in the range from 150 but no more than 300 and the silicalite shell, and said catalyst has the weight ratio of shell to core greater than 0 but less than or equal to 2.

In one aspect of the invention, said catalyst comprises the ferrierite core having the mole ratio of silica to alumina in the range from 50 but no more than 150 and the silicalite shell, and said catalyst has the weight ratio of shell to core greater than 0 but less than or equal to 2.

In one aspect of the invention, said catalyst further comprises manganese (Mn).

In one aspect of the invention, said catalyst further comprises manganese (Mn), wherein said manganese is in an amount of from 1 to 15% by weight when comparing with the weight of zeolite core. Preferably, said manganese is in an amount of from 5 to 10% by weight when comparing with the weight of zeolite core.

In one aspect of the invention, said zeolite core further comprises manganese (Mn).

In one aspect of the invention, said zeolite core further comprises manganese (Mn), wherein said manganese is in an amount of from 1 to 15% by weight when comparing with the weight of zeolite core. Preferably, said manganese is in an amount of from 5 to 10% by weight when comparing with the weight of zeolite core.

In one aspect of the invention, said hydrocarbon is selected from butane, pentane, hexane, or heptane. Preferably, said hydrocarbon is butane, most preferably isobutane.

In one aspect of the invention, said light olefins are ethylene and propylene.

In one aspect of the invention, the catalyst as described above is used for the process of light olefins production from catalytic cracking of hydrocarbon having 4 to 7 carbon atoms, preferably hydrocarbon having 4 carbon atom selected from, but not limited to butane.

In another aspect of the invention, the process for preparing the catalyst for light olefins production from catalytic cracking of hydrocarbon having 4 to 7 carbon atoms may comprise the following steps:

a) preparing the mixture comprising the compound for preparing the first zeolite and the first soft structure-directing agent, and subjecting to the hydrothermal process at the determined temperature and time in order to transform said mixture into zeolite; and b) preparing the mixture comprising the compound for preparing the silicalite, the second soft structure-directing agent, and the zeolite obtained from step a), and subjecting to the hydrothermal process at the determined temperature and time in order to transform said mixture into zeolite having the core-shell structure.

In one aspect of the invention, each step of said process for preparing the catalyst may further comprise the calcination step at the temperature in the range from 400 to 650° C.

In one aspect of the invention, said process for preparing the catalyst may further comprise the drying step.

Drying may be performed by conventional drying method using oven, vacuum drying, stirred evaporation, and drying by rotary evaporator.

In one aspect of the invention, each step of said process for preparing the catalyst may further comprise the ion exchange by contacting with ammonium salt solution.

In one aspect of the invention, said ammonium salt solution is selected from, but not limited to ammonium nitrate ($NH_4NO_3$) or ammonium hydroxide.

In one aspect of the invention, the compound for preparing the first zeolite is the mixture of alumina compound selected from aluminium isopropoxide, sodium aluminate, aluminium sulfate, aluminium nitrate, or aluminum hydroxide, and silica compound selected from tetraethyl orthosilicate (TEOS), sodium silicate, or silica gel.

In one aspect of the invention, said first soft structure-directing agent is selected from pyrrolidine, quaternary ammonium salt containing silane group, or quaternary ammonium salt. In one aspect of the invention, quaternary ammonium salt containing silane group may be selected from, but not limited to 3-(trimethoxysilyl)-propyl-octadecyl-dimethyl-ammonium chloride (TPOAC).

In one aspect of the invention, said quaternary ammonium salt may be selected from, but not limited to tetraalkylammonium salt selected from tetrapropylammonium hydroxide, tetrapropylammonium bromide, or tetrabutylammonium hydroxide.

In one aspect of the invention, said quaternary ammonium salt may further comprise long-chain quaternary ammonium surfactant that may be selected from, but not limited to cetyltrimethylammonium bromide (CTAB) or cetyltrimethylammonium chloride (CTAC).

In one aspect of the invention, said compound for preparing the silicalite may be selected from, but not limited to tetraethyl orthosilicate, sodium silicate, or silica gel.

In one aspect of the invention, said second soft structure-directing agent is selected from quarterly phosphonium salt or mixture of the quaternary ammonium salt further comprising long-chain quaternary ammonium surfactant.

In one aspect of the invention, said quarterly phosphonium salt is selected from tetrabutylphosphonium hydroxide (TBPOH) or tributyl hexadecyl phosphonium bromide.

In one aspect of the invention, mixture of the quaternary ammonium salt further comprising long-chain quaternary ammonium surfactant, wherein said quaternary ammonium salt may be selected from, but not limited to tetraalkylammonium salt selected from tetrapropylammonium hydroxide, tetrapropylammonium bromide, or tetrabutylammonium hydroxide.

In one aspect of the invention, mixture of the quaternary ammonium salt further comprising long-chain quaternary ammonium surfactant, wherein said long-chain quaternary ammonium surfactant may be selected from, but not limited to cetyltrimethylammonium bromide (CTAB) or cetyltrimethylammonium chloride (CTAC).

In another aspect of the invention, this invention relates to the process of light olefins production from catalytic cracking of hydrocarbon having 4 to 7 carbon atoms, comprising the contact of the hydrocarbon having 4 to 7 carbon atoms to the catalyst at the temperature in the range from 400 to 700° C. and the pressure in the range from about 0.1 to 10 bars, wherein said catalyst is selected from the catalyst according to the invention as described above or the catalyst obtained from the process for preparing the catalyst as described above.

In one aspect of the invention, the contact of the hydrocarbon having 4 to 7 carbon atoms to the catalyst is performed at the temperature in the range from 500 to 700° C., preferably at the temperature in the range from 550 to 680° C.

In one aspect of the invention, the contact of the hydrocarbon having 4 to 7 carbon atoms to the catalyst is performed at the pressure in the range from about 1 to 10 bars, preferably at the pressure in the range from about 1 to 7 bars.

In one aspect of the invention, said hydrocarbon is selected from butane, pentane, hexane, or heptane. Preferably, said hydrocarbon is butane, most preferably iso-butane. In one aspect of the invention, the products obtained from the catalytic cracking of hydrocarbon having 4 to 7 carbon atoms are the light olefins, preferably ethylene and propylene.

In one aspect of the invention, the process of light olefins production from catalytic cracking may be performed in the reactor but not limited to the fixed-bed reactor which may be performed in batch or continuous manner, or may be performed in fixed bed system, moving bed system, fluidized bed system, or batch system.

The weight hourly space velocity (WHSV) of the feed line of the hydrocarbon in the catalytic cracking is in the range of about 1 to 50 per hour, preferably in the range of about 1.5 to 16 per hour.

Generally, any person skilled in this art can adjust the condition of catalytic cracking of hydrocarbon having 4 to 7 carbon atoms to be suitable for type and composition of feed line, catalyst, and reactor system.

The following examples are only for demonstrating one aspect of this invention, not for limiting the scope of this invention in any way.

Preparation of the Catalyst

The preparation of the catalyst may be performed by the following methods.

Preparation of the Ferrierite (FER) Zeolite Catalyst

The preparation of the ferrierite zeolite catalyst could be prepared by hydrothermal method using pyrrolidine as the structure-directing agent of the zeolite as follows.

The first solution comprising sodium silicate, pyrrolidine, and water and the second solution comprising aluminium sulfate, concentrated sulfuric acid, and water were prepared. Then, the second solution was dropped into the first solution under continuous stirring. After that, said obtained mixture was subjected to the hydrothermal process at the temperature about 130 to 180° C. in order to transform said mixture into zeolite.

Then, the obtained zeolite was washed with deionized water, dried, and calcinated at the temperature about 500 to 650° C. to obtain zeolite which was white powder.

After that, said zeolite was subjected to the ion exchange by contacting the obtained zeolite with 1 M ammonium nitrate ($NH_4NO_3$) solution at the temperature about 60 to 90° C. under continuous stirring. Then, it was washed with deionized water, dried, and calcinated at the temperature about 500 to 600° C. to obtain the ferrierite zeolite catalyst.

Preparation of the ZSM-5 Zeolite Catalyst

The preparation of the ZSM-5 zeolite catalyst could be prepared by hydrothermal method using tetrapropylammonium hydroxide (TPAOH) as the structure-directing agent of the zeolite and cetyltrimethylammonium bromide (CTAB) as the agent for making hierarchical pores as follows.

The first solution comprising tetraethyl orthosilicate (TEOS) and the second solution comprising aluminium hydroxide, tetrapropylammonium hydroxide, sodium hydroxide, cetyltrimethylammonium bromide, and water were prepared. Then, the second solution was dropped into the first solution under continuous stirring. After that, said obtained mixture was subjected to the hydrothermal process at the temperature about 100 to 180° C. in order to transform said mixture into zeolite.

Then, the obtained zeolite was washed with deionized water, dried, and calcinated at the temperature about 500 to 650° C. to obtain zeolite which was white powder.

After that, said zeolite was subjected to the ion exchange by contacting the obtained zeolite with 1 M ammonium nitrate ($NH_4NO_3$) solution at the temperature about 60 to 90° C. under continuous stirring. Then, it was washed with deionized water, dried, and calcinated at the temperature about 500 to 600° C. to obtain the ZSM-5 zeolite catalyst having hierarchical pores.

Preparation of the Silicalite Catalyst

The preparation of the silicalite catalyst having silica to alumina ratio of infinity ($SiO_2/Al_2O_3=\infty$) could be prepared by hydrothermal method using tetrabutylphosphonium hydroxide (TBPOH) as the structure-directing agent of the zeolite and nanosheet structure as follows.

The first solution comprising tetraethyl orthosilicate (TEOS) and the second solution comprising tetrabutylphosphonium hydroxide, sodium hydroxide, and water were prepared. Then, the second solution was dropped into the first solution under continuous stirring. After that, said obtained mixture was subjected to the hydrothermal process at the temperature about 100 to 200° C. in order to transform said mixture into zeolite.

Then, the obtained zeolite was washed with deionized water, dried, and calcinated at the temperature about 500 to 650° C. to obtain zeolite which was white powder.

After that, said zeolite was subjected to the ion exchange by contacting the obtained zeolite with 1 M ammonium nitrate ($NH_4NO_3$) solution at the temperature about 60 to 90° C. under continuous stirring. Then, it was washed with deionized water, dried, and calcinated at the temperature about 500 to 600° C. to obtain the silicalite catalyst having hierarchical pores, wherein said silicalite catalyst having hierarchical pores was arranged in nano-sheet.

Preparation of the Ferrierite Zeolite Catalyst Comprising Manganese (Mn)

The preparation of the ferrierite zeolite catalyst comprising manganese (Mn) could be prepared by hydrothermal method using the preparation process of the ferrierite zeolite catalyst as described above and the addition of manganese sulfate into the mixture in the step before subjecting the mixture to the hydrothermal process.

Preparation of the Catalyst Having Core-Shell Structure

The preparation of the catalyst having core-shell structure could be prepared by hydrothermal method as follows.

The first solution and the second solution were prepared. Then, the second solution was dropped into the first solution under continuous stirring. Then, the zeolite catalyst being used as the core was added under continuous stirring at room temperature. After that, said obtained mixture was subjected to the hydrothermal process at the temperature about 100 to 200° C. in order to transform said mixture into zeolite.

Then, the obtained zeolite was washed with deionized water, dried, and calcinated at the temperature about 500 to 650° C. to obtain zeolite which was white powder.

After that, said zeolite was subjected to the ion exchange by contacting the obtained zeolite with 1 M ammonium nitrate ($NH_4NO_3$) solution at the temperature about 60 to 90° C. under continuous stirring. Then, it was washed with deionized water, dried, and calcinated at the temperature about 500 to 600° C. to obtain the catalyst having core-shell structure.

Preparation of the Comparative Catalyst and the Catalyst According to the Invention Comparative Catalyst CAT A The comparative catalyst CAT A could be prepared using the preparation process of the ferrierite zeolite catalyst as described above. Said comparative catalyst had the mole ratio of silica to alumina of about 61.

Comparative Catalyst CAT B

The comparative catalyst CAT B could be prepared using the preparation process of the ZSM-5 zeolite catalyst as described above. Said comparative catalyst had the mole ratio of silica to alumina of about 143.

Comparative Catalyst CAT C

The comparative catalyst CAT C could be prepared using the preparation process of the silicalite catalyst as described above.

Comparative Catalyst CAT D

The comparative catalyst CAT D was the catalyst having core-shell structure, wherein the shell was ferrierite zeolite and said core-shell structure had the weight ratio of shell to core of about 1. The comparative catalyst CAT D could be prepared using the preparation process of the catalyst having core-shell structure as described above. Pyrrolidine was used as the structure-directing agent of the zeolite. The first solution comprising sodium silicate, pyrrolidine, and water and the second solution comprising aluminium sulfate, concentrated sulfuric acid, and water were prepared. The zeolite catalyst being used as the core was the comparative catalyst CAT B having the mole ratio of silica to alumina of about 143. While said ferrierite zeolite shell was prepared at the mole ratio of silica to alumina of about 60.

Comparative Catalyst CAT E

The comparative catalyst CAT E was the catalyst having core-shell structure, wherein the shell was ZSM-5 zeolite having hierarchical pores and said core-shell structure had the weight ratio of shell to core of about 1. The comparative catalyst CAT E could be prepared using the preparation process of the catalyst having core-shell structure as described above. Tetrapropylammonium hydroxide (TPAOH) was used as the structure-directing agent of the zeolite and cetyltrimethylammonium bromide (CTAB) was used as the agent for making hierarchical pores. The first solution comprising tetraethyl orthosilicate (TEOS) and the second solution comprising aluminium hydroxide, tetrapropylammonium hydroxide, sodium hydroxide, cetyltrimethylammonium bromide, and water were prepared. The zeolite catalyst being used as the core was the comparative catalyst CAT A having the mole ratio of silica to alumina of about 61. While said ZSM-5 zeolite shell having hierarchical pores was prepared at the mole ratio of silica to alumina of about 160.

Comparative Catalyst CAT F

The comparative catalyst CAT F was the catalyst having core-shell structure, wherein the shell was the conventional silicalite having silica to alumina ratio of infinity ($SiO_2/Al_2O_3=\infty$) and said core-shell structure had the weight ratio of shell to core of about 1. The comparative catalyst CAT F could be prepared using the preparation process of the catalyst having core-shell structure as described above. Tetrapropylammonium hydroxide (TPAOH) was used as the structure-directing agent of the zeolite. The first solution comprising silica and tetrapropylammonium hydroxide solutions and the second solution comprising sodium hydroxide were prepared. The zeolite catalyst being used as the core was the comparative catalyst CAT A having the mole ratio of silica to alumina of about 61.

Comparative Catalyst CAT G

The comparative catalyst CAT G was the catalyst having core-shell structure, wherein the shell was silicalite having hierarchical pores that was arranged in nano-sheet and having silica to alumina ratio of infinity ($SiO_2/Al_2O_3=\infty$) and said core-shell structure had the weight ratio of shell to core of about 4. The comparative catalyst CAT G could be prepared using the preparation process of the catalyst having core-shell structure as described above. Tetrabutylphosphonium hydroxide (TBPOH) was used as the structure-directing agent of the zeolite and nanosheet structure. The first solution comprising tetraethyl orthosilicate (TEOS) and the second solution comprising tetrabutylphosphonium hydroxide, sodium hydroxide, and water were prepared. The zeolite catalyst being used as the core was the comparative catalyst CAT A having the mole ratio of silica to alumina of about 61.

Comparative Catalyst CAT H

The comparative catalyst CAT H was the catalyst having core-shell structure, wherein the shell was the conventional silicalite having silica to alumina ratio of infinity ($SiO_2/Al_2O_3=\infty$) and said core-shell structure had the weight ratio of shell to core of about 1. The comparative catalyst CAT H could be prepared using the preparation process of the catalyst having core-shell structure as described above. Tetrapropylammonium hydroxide (TPAOH) was used as the structure-directing agent of the zeolite. The first solution comprising silica and tetrapropylammonium hydroxide solutions and the second solution comprising sodium hydroxide were prepared. The zeolite catalyst being used as the core was the comparative catalyst CAT B having the mole ratio of silica to alumina of about 143.

Comparative Catalyst CAT I

The comparative catalyst CAT I was the catalyst having core-shell structure, wherein the shell was the conventional silicalite having silica to alumina ratio of infinity ($SiO_2/Al_2O_3=\infty$) and said core-shell structure had the weight ratio of shell to core of about 1. Moreover, the catalyst was further comprised manganese in the amount of about 5% by weight when comparing with the weight of zeolite core. The comparative catalyst CAT I could be prepared using the preparation process of the catalyst having core-shell structure as described above. Tetrapropylammonium hydroxide (TPAOH) was used as the structure-directing agent of the zeolite. The first solution comprising silica and tetrapropylammonium hydroxide solutions and the second solution comprising sodium hydroxide were prepared. The zeolite catalyst being used as the core was the catalyst prepared from the preparation process of the ferrierite zeolite catalyst comprising manganese (Mn) as described above. Said ferrierite zeolite catalyst comprising manganese had the mole ratio of silica to alumina of about 72.

Catalyst According to the Invention CAT 1

The catalyst according to the invention CAT 1 was the catalyst having core-shell structure, wherein the shell was silicalite having hierarchical pores that was arranged in nano-sheet and having silica to alumina ratio of infinity ($SiO_2/Al_2O_3=\infty$) and said core-shell structure had the weight ratio of shell to core of about 1. The catalyst according to the invention CAT 1 could be prepared using the preparation process of the catalyst having core-shell structure as described above. Tetrabutylphosphonium hydroxide (TBPOH) was used as the structure-directing agent of the zeolite and nanosheet structure. The first solution comprising tetraethyl orthosilicate (TEOS) and the second solution comprising tetrabutylphosphonium hydroxide, sodium hydroxide, and water were prepared. The zeolite catalyst being used as the core was the comparative catalyst CAT A having the mole ratio of silica to alumina of about 61.

Catalyst According to the Invention CAT 2

The catalyst according to the invention CAT 2 was the catalyst having core-shell structure, wherein the shell was silicalite having hierarchical pores that was arranged in nano-sheet and having silica to alumina ratio of infinity ($SiO_2/Al_2O_3=\infty$) and said core-shell structure had the weight ratio of shell to core of about 2. The catalyst according to the invention CAT 2 could be prepared using the preparation process of the catalyst having core-shell structure as described above. Tetrabutylphosphonium hydroxide (TBPOH) was used as the structure-directing agent of the zeolite and nanosheet structure. The first solution comprising tetraethyl orthosilicate (TEOS) and the second solution comprising tetrabutylphosphonium hydroxide, sodium hydroxide, and water were prepared. The zeolite catalyst being used as the core was the comparative catalyst CAT A having the mole ratio of silica to alumina of about 61.

Catalyst According to the Invention CAT 3

The catalyst according to the invention CAT 3 was the catalyst having core-shell structure, wherein the shell was silicalite having hierarchical pores that was arranged in nano-sheet and having silica to alumina ratio of infinity ($SiO_2/Al_2O_3=\infty$) and said core-shell structure had the weight ratio of shell to core of about 2. The catalyst according to the invention CAT 3 could be prepared using the preparation process of the catalyst having core-shell structure as described above. Tetrabutylphosphonium hydroxide (TBPOH) was used as the structure-directing agent of the zeolite and nanosheet structure. The first solution comprising tetraethyl orthosilicate (TEOS) and the second solution comprising tetrabutylphosphonium hydroxide, sodium hydroxide, and water were prepared. The zeolite catalyst being used as the core was the ZSM-5 zeolite catalyst prepared from the preparation process of the ZSM-5 zeolite catalyst as described above. Said ZSM-5 zeolite catalyst had the mole ratio of silica to alumina of about 104.

Catalyst According to the Invention CAT 4

The catalyst according to the invention CAT 4 was the catalyst having core-shell structure, wherein the shell was silicalite having hierarchical pores that was arranged in nano-sheet and having silica to alumina ratio of infinity ($SiO_2/Al_2O_3=\infty$) and said core-shell structure had the weight ratio of shell to core of about 1. The catalyst according to the invention CAT 4 could be prepared using the preparation process of the catalyst having core-shell structure as described above. Tetrabutylphosphonium hydroxide (TBPOH) was used as the structure-directing agent of the zeolite and nanosheet structure. The first solution comprising tetraethyl orthosilicate (TEOS) and the second solution comprising tetrabutylphosphonium hydroxide, sodium hydroxide, and water were prepared. The zeolite catalyst being used as the core was the comparative catalyst CAT B having the mole ratio of silica to alumina of about 143.

Catalyst According to the Invention CAT 5

The catalyst according to the invention CAT 5 was the catalyst having core-shell structure, wherein the shell was silicalite having hierarchical pores that was arranged in nano-sheet and having silica to alumina ratio of infinity ($SiO_2/Al_2O_3=\infty$) and said core-shell structure had the weight ratio of shell to core of about 2. The catalyst according to the invention CAT 5 could be prepared using the preparation process of the catalyst having core-shell structure as described above. Tetrabutylphosphonium hydroxide (TBPOH) was used as the structure-directing agent of the zeolite and nanosheet structure. The first solution comprising tetraethyl orthosilicate (TEOS) and the second solution comprising tetrabutylphosphonium hydroxide, sodium hydroxide, and water were prepared. The zeolite catalyst being used as the core was the comparative catalyst CAT B having the mole ratio of silica to alumina of about 143.

Catalyst According to the Invention CAT 6

The catalyst according to the invention CAT 6 was the catalyst having core-shell structure, wherein the shell was silicalite having hierarchical pores that was arranged in nano-sheet and having silica to alumina ratio of infinity ($SiO_2/Al_2O_3=\infty$) and said core-shell structure had the weight ratio of shell to core of about 1. Moreover, the catalyst was further comprised manganese in the amount of about 5% by weight when comparing with the weight of zeolite core. The catalyst according to the invention CAT 6 could be prepared using the preparation process of the catalyst having core-shell structure as described above. Tetrabutylphosphonium hydroxide (TBPOH) was used as the structure-directing agent of the zeolite and nanosheet structure. The first solution comprising tetraethyl orthosilicate (TEOS) and the second solution comprising tetrabutylphosphonium hydroxide, sodium hydroxide, and water were prepared. The zeolite catalyst being used as the core was the catalyst prepared from the preparation process of the ferrierite zeolite catalyst comprising manganese (Mn) as described above. Said ferrierite zeolite catalyst comprising manganese had the mole ratio of silica to alumina of about 72.

Catalyst According to the Invention CAT 7

The catalyst according to the invention CAT 7 was the catalyst having core-shell structure, wherein the shell was silicalite having hierarchical pores that was arranged in nano-sheet and having silica to alumina ratio of infinity ($SiO_2/Al_2O_3=\infty$) and said core-shell structure had the weight ratio of shell to core of about 1. Moreover, the catalyst was further comprised manganese in the amount of about 5% by weight when comparing with the weight of zeolite core. The catalyst according to the invention CAT 7 could be prepared using impregnation method of magnesium sulfate onto the catalyst according to the invention CAT 1 and then calcination at the temperature about 500 to 600° C.

Testing for the Catalytic Cracking of Hydrocarbon Having 4 to 7 Carbon Atoms to Produce Light Olefins The testing for the catalytic cracking of hydrocarbon having 4 to 7 carbon atoms for light olefins production might be performed using the following conditions.

The catalytic cracking was performed in the fixed-bed reactor using about 0.3 g of the catalyst. Prior to the reaction, the catalyst was contacted with hydrogen gas having the flow rate of about 50 mL/min for about 3 hours. Then, the hydrocarbon having 4 carbon atom, that is 99% iso-butane, were fed at the flow rate of about 10 mL/min together with nitrogen gas at the flow rate of 20 mL/min. The reaction was employed at the temperature about 600 to 650° C. at the atmospheric pressure and the weight hourly space velocity (WHSV) of about 5 per hour.

Then, the reaction was monitored by measuring the conversion of the reactant and the formation of the product composition after passing the catalyst at different reaction times using gas chromatography connected to the outlet of the fixed-bed reactor. The detector used was flame ionization detector (FID) and the column used was the HP Innowax and a HP-Plot $Al_2O_3$ capillary column for the separation and analysis of each composition of said substances.

From FIG. 1 that shows the characteristics of crystalline structure tested by scanning electron microscope (SEM) technique at accelerating voltage of 20 kV using SEI mode, it shows that the comparative catalyst CAT A used as the core in the catalyst according to the invention had flower shape-like particle arrangement and had the porosity which was different from the commercial ferrierite zeolite, whereas the comparative catalyst CAT B used as the core in the catalyst according to the invention had hierarchical pores and clearly organized porosity which was different from the conventional ZSM-5 zeolite. When considering the catalysts according to the invention having core-shell structure, it was found that the surface of the catalysts according to the invention had hierarchical pores and beautiful and organized porosity more than the comparative catalysts.

From the testing of the specific surface area of micropores, mesopores, and macropores as shown in Table 1, it was found that the catalysts according to the invention had the proportion of volume of mesopores and macropores to the total pore volume in the range from 0.35 to 0.90. When comparing with the comparative catalyst having core-shell structure in which the shell was the conventional silicalite, it was found that the catalyst according to the invention having core-shell structure in which the shell was silicalite having hierarchical pores that was arranged in nano-sheet had the proportion of volume of mesopores and macropores to the total pore volume more than the comparative catalyst having core-shell structure in which the shell was the conventional silicalite.

Figure 2:
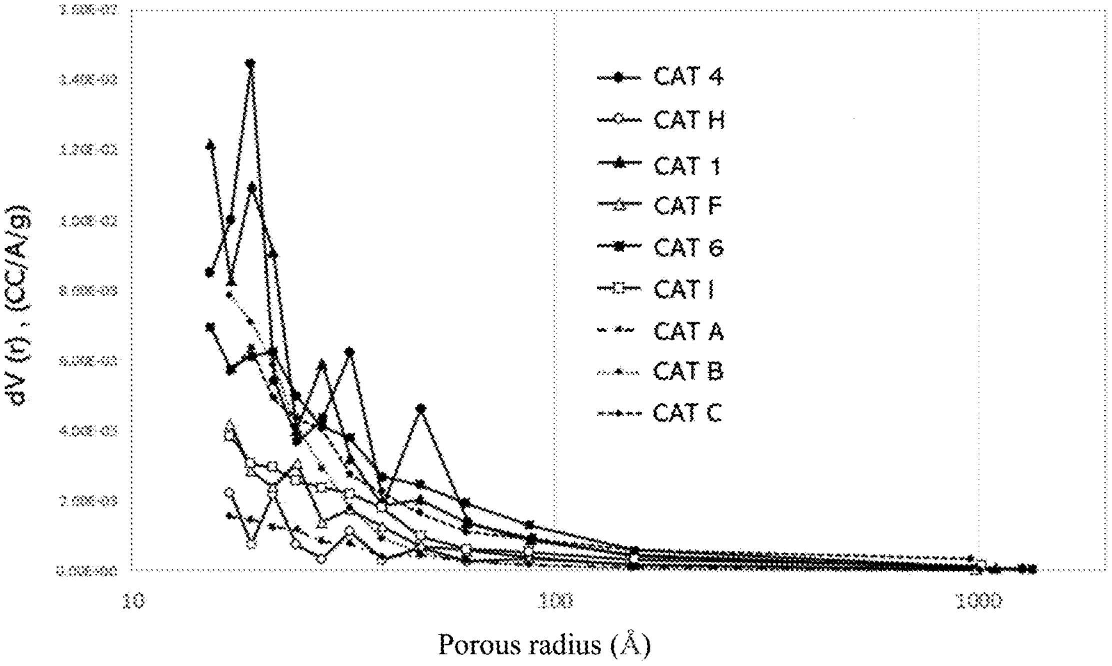
FIG. 2 shows the pore size distribution analyzed by Barrett-Joyner-Halenda adsorption (BJH adsorption).

When considering the pore size distribution analyzed by Barrett-Joyner-Halenda adsorption (BJH adsorption), it was found that the results of pore size distribution are shown in FIG. 2 and Table 2. The catalyst according to the invention had clearly different distribution of mesopores and macropores from the comparative catalyst. The catalysts according to the invention had the pore size distribution of mesopores having pore size in the range of 2 to 5 nm mostly and further comprised mesopores having pore size in the range of 5 to 8 nm and in the range of 8 to 18 nm. The catalyst according to the invention gave the proportion of volume of mesopores having pore size in each range to the total pore volume more than the comparative catalyst.

To study the effect of the structure of catalyst having core-shell structure comprising zeolite core selected from ferrierite, ZSM-5, or mixture thereof, and silicalite shell having MFI structure on the efficacy of light olefins production from catalytic cracking of hydrocarbon having 4 to 7 carbon atoms, the catalysts according to the invention were studied and compared with the comparative catalysts. Results were shown in FIG. 3 to FIG. 6.

Figure 3:
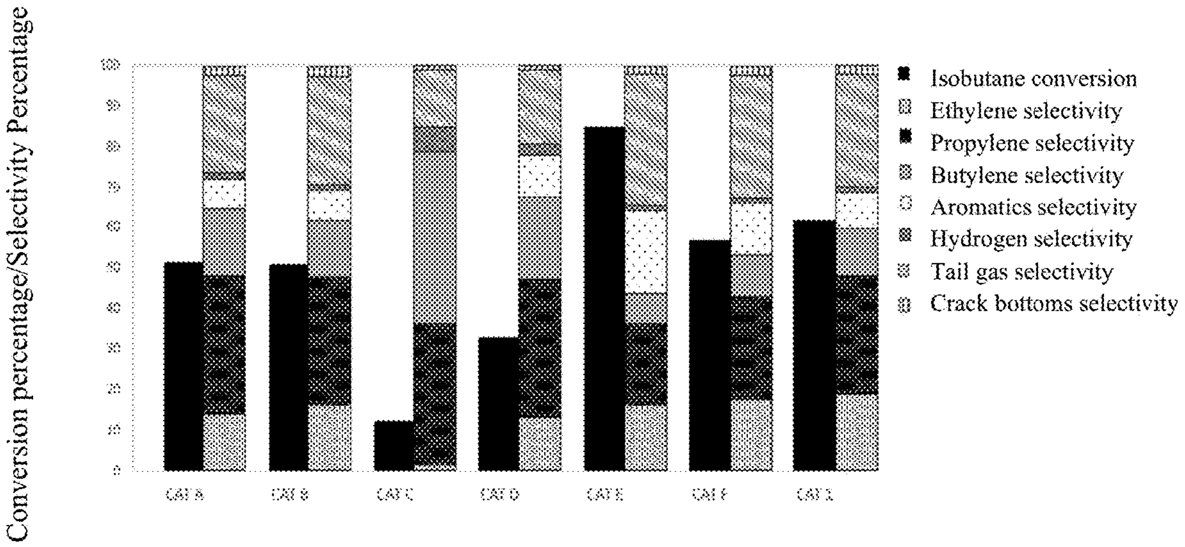
FIG. 3 shows the conversion of the reactant and the selectivity to each product of different catalysts in the catalytic cracking of isobutane.

FIG. 3 shows the conversion of the reactant and the selectivity to each product of different catalysts in the catalytic cracking of butane. It was found that the catalyst according to the invention gave better efficacy than the comparative samples, providing both of high selectivity to light olefins and high conversion of the reactant.

Figure 4:
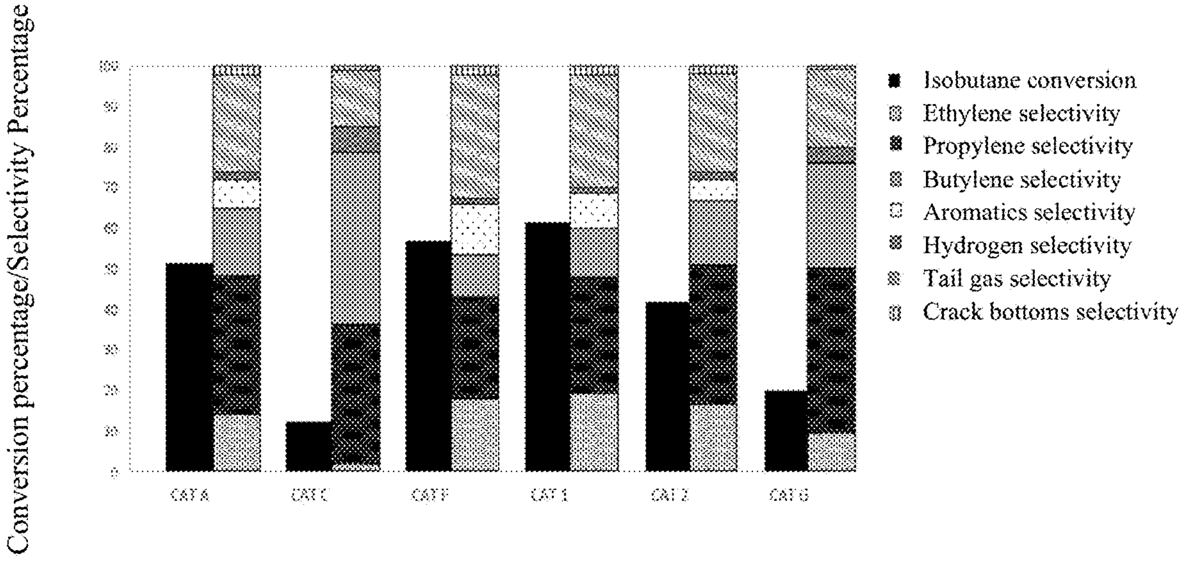
FIG. 4 shows the conversion of the reactant and the selectivity to each product of the catalysts having core-shell structure in which the zeolite core was the ferrierite comparing with the comparative sample catalysts in the catalytic cracking of isobutane.

FIG. 4 shows the conversion of the reactant and the selectivity to each product of the catalysts having core-shell structure in which the zeolite core was the ferrierite comparing with the comparative sample catalysts in the catalytic cracking of butane. It was found that the catalysts according to the invention gave better efficacy than the comparative samples, providing increased selectivity to light olefins. In addition, the weight ratio of shell to core was the factor affecting the conversion of the reactant. It could help to increase the conversion of the reactant without decreasing the selectivity to light olefins.

Figure 5:
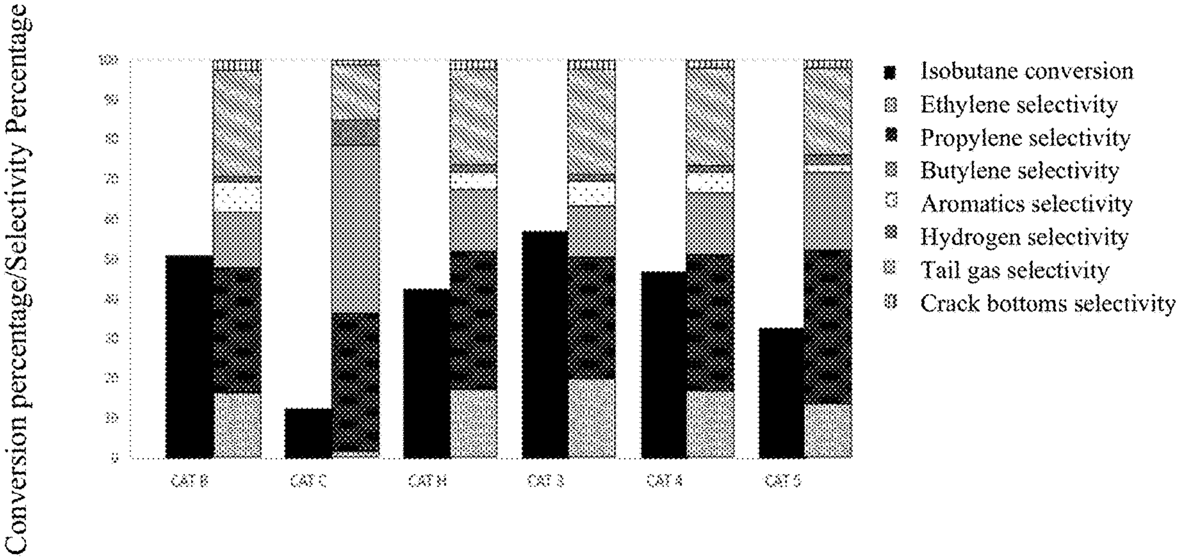
FIG. 5 shows the conversion of the reactant and the selectivity to each product of the catalyst having core-shell structure in which the zeolite core was the ZSM-5 comparing with the comparative sample catalysts in the catalytic cracking of isobutane.

FIG. 5 shows the conversion of the reactant and the selectivity to each product of the catalysts having core-shell structure in which the zeolite core was the ZSM-5 comparing with the comparative sample catalysts in the catalytic cracking of butane. It was found that the catalysts according to the invention gave better efficacy than the comparative samples, providing higher selectivity to light olefins. In addition, the mole ratio of silica to alumina of ZSM-5 and the weight ratio of shell to core were the factors affecting the conversion of the reactant. This could help to increase the conversion of the reactant.

Figure 6:
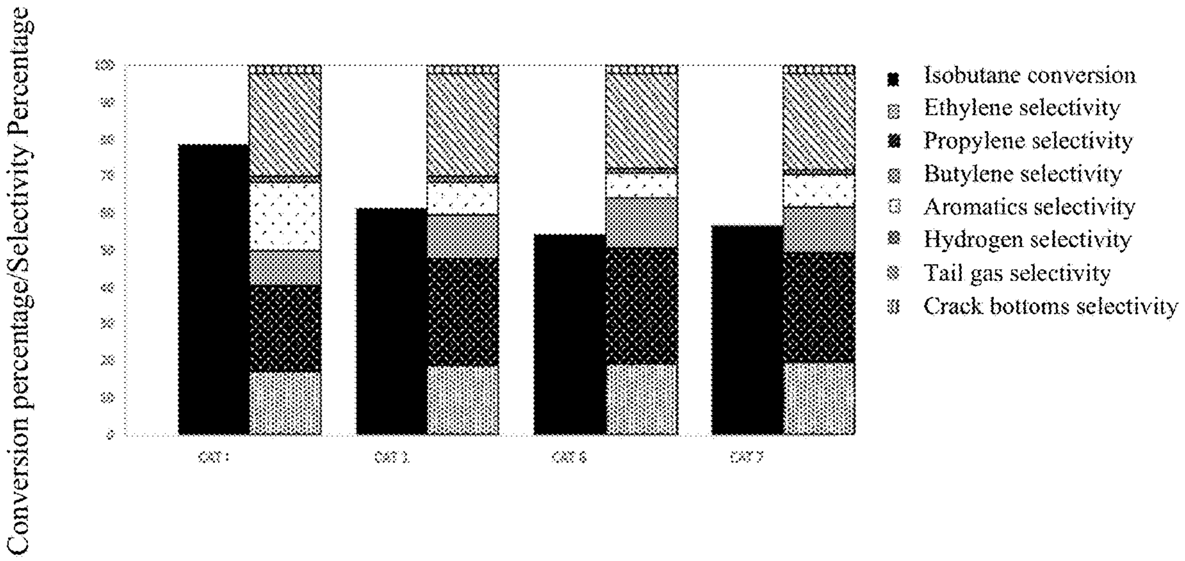
FIG. 6 shows the conversion of the reactant and the selectivity to each product of the catalysts having the manganese addition in different ways comparing with the comparative sample catalyst in the catalytic cracking of isobutane.

FIG. 6 shows the conversion of the reactant and the selectivity to each product of the catalysts having the manganese (Mn) addition in different ways comparing with the comparative sample catalyst in the catalytic cracking of butane. It was found that the catalysts according to the invention showed increased selectivity to light olefins when comparing with the comparative sample.

From the experimental results above, it could be said that the catalysts having core-shell structure according to the invention gave high conversion of the reactant and especially high selectivity to light olefins product for the catalytic cracking of hydrocarbon having 4 to 7 carbon atoms as stated in the objective of this invention.

TABLE 1

Mole ratio of silica to alumina, specific surface area, and porosity properties of the comparative samples and samples according to the invention

| Sample | Mole ratio of silica to alumina | BET specific surface area ($S_{BET}$) ($m^2/g$) | External specific surface area ($S_{ext}$) ($m^2/g$) | Proportion of volume of mesopores and macropores to total pore volume |
|---|---|---|---|---|
| CAT A | 61 | 297 | 60 | 0.38 |
| CAT B | 143 | 436 | 83 | 0.37 |
| CAT C | α | 359 | 117 | 0.82 |
| CAT E | 87 | 364 | 47 | 0.47 |
| CAT F | 116 | 424 | 58 | 0.50 |
| CAT G | 484 | 580 | 124 | 0.57 |
| CAT H | | 301 | 30 | 0.49 |
| CAT I | 136 | 368 | 70 | 0.70 |
| CAT 1 | 130 | 592 | 177 | 0.66 |
| CAT 2 | 173 | 534 | 100 | 0.45 |
| CAT 3 | 241 | 610 | 100 | 0.40 |
| CAT 4 | 352 | 485 | 179 | 0.70 |
| CAT 5 | 528 | 532 | 134 | 0.61 |
| CAT 6 | 220 | 514 | 145 | 0.66 |
| CAT 7 | 173 | 486 | 112 | 0.64 |

Note:
BET specific surface area ($S_{BET}$) and total pore volume ($V_{total}$) were obtained from $N_2$ physisorption; $S_{ext}$: external specific surface area; $V_{meso+macro}$: mesopore volume and macropore volume were calculated from the BJH adsorption analysis.

TABLE 2

Pore size distribution analyzed by Barrett-Joyner-Halenda adsorption (BJH adsorption) of the comparative samples and samples according to the invention

| Sample | Volume of pores having pore size of 2-5 nm to total pore volume | Volume of pores having pore size of 5-8 nm to total pore volume | Volume of pores having pore size of 8-18 nm to total pore volume |
|---|---|---|---|
| CAT F | 0.08 | 0.06 | 0.08 |
| CAT G | 0.13 | 0.08 | 0.09 |
| CAT H | 0.05 | 0.04 | 0.09 |
| CAT I | 0.06 | 0.07 | 0.08 |
| CAT 1 | 0.16 | 0.08 | 0.12 |
| CAT 2 | 0.15 | 0.09 | 0.06 |
| CAT 3 | 0.15 | 0.07 | 0.07 |

TABLE 2-continued

Pore size distribution analyzed by Barrett-Joyner-Halenda adsorption (BJH adsorption) of the comparative samples and samples according to the invention

| Sample | Volume of pores having pore size of 2-5 nm to total pore volume | Volume of pores having pore size of 5-8 nm to total pore volume | Volume of pores having pore size of 8-18 nm to total pore volume |
|---|---|---|---|
| CAT 4 | 0.17 | 0.12 | 0.19 |
| CAT 5 | 0.13 | 0.12 | 0.14 |
| CAT 6 | 0.12 | 0.10 | 0.18 |
| CAT 7 | 0.10 | 0.09 | 0.14 |

BEST MODE OF THE INVENTION

Best mode or preferred embodiment of the invention is as provided in the description of the invention.

What is claimed is:

1. A catalyst for light olefins production from catalytic cracking of hydrocarbon having 4 to 7 carbon atoms, wherein said catalyst has a core-shell structure comprising zeolite core selected from ferrierite, ZSM-5, or mixture thereof, and silicalite shell having MFI structure, and said catalyst has the following characteristics:

a) the weight ratio of shell to core greater than 0 but less than 4;

b) the mole ratio of silica to alumina ($SiO_2/Al_2O_3$) from 60 to 550;

c) the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.35 to 0.90, and said mesopores comprise pores having pore size from 2 to 5 nm, wherein the proportion of volume of pores having pore size from 2 to 5 nm to the total pore volume is in the range from 0.08 to 0.30.

2. The catalyst according to claim 1, wherein said mesopores comprise pores having pore size from 2 to 5 nm, wherein the proportion of volume of pores having pore size from 2 to 5 nm to the total pore volume is in the range from 0.10 to 0.20.

3. The catalyst according to claim 1, wherein said mesopores further comprise pores having pore size from 5 to 8 nm and pores having pore size from 8 to 18 nm.

4. The catalyst according to claim 1, wherein said zeolite core has the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.30 to 0.90.

5. The catalyst according to claim 1, wherein said zeolite core has the hierarchical pores and is arranged in nano-sheet.

6. The catalyst according to claim 1, wherein said silicalite shell has the hierarchical pores and is arranged in nano-sheet.

7. The catalyst according to claim 1, wherein said zeolite core has the mole ratio of silica to alumina in the range from 35 to 320.

8. The catalyst according to claim 1, wherein said zeolite core is the ferrierite having the flower shape-like particle arrangement when analyzed by the scanning electron microscope (SEM) technique at the accelerating voltage of 20 kV with SEI mode.

9. The catalyst according to claim 1, wherein said catalyst has the mole ratio of silica to alumina in the range from 100 to 400.

10. The catalyst according to claim 1, wherein said catalyst comprises the ZSM-5 core having the mole ratio of silica to alumina in the range from 120 to 300 and the silicalite shell, and said catalyst has the weight ratio of shell to core greater than 0 but less than or equal to 1.5.

11. The catalyst according to claim 1, wherein said catalyst comprises the ZSM-5 core having the mole ratio of silica to alumina in the range from 50 to 120 and the silicalite shell, and said catalyst has the weight ratio of shell to core greater than 0 but less than or equal to 3.

12. The catalyst according to claim 1, wherein said catalyst comprises the ferrierite core having the mole ratio of silica to alumina in the range from 150 to 300 and the silicalite shell, and said catalyst has the weight ratio of shell to core greater than 0 but less than or equal to 2.

13. The catalyst according to claim 12, wherein said catalyst further comprises manganese (Mn) in an amount of from 1 to 15% by weight when comparing with the weight of zeolite core.

14. The catalyst according to claim 1, wherein said catalyst comprises the ferrierite core having the mole ratio of silica to alumina in the range from 50 to 150 and the silicalite shell, and said catalyst has the weight ratio of shell to core greater than 0 but less than or equal to 2.

15. The catalyst according to claim 1, wherein said catalyst further comprises manganese (Mn).

16. The catalyst according to claim 15, wherein said zeolite core further comprises manganese (Mn) in an amount of from 1 to 15% by weight when comparing with the weight of zeolite core.

17. The catalyst according to claim 1, wherein said zeolite core further comprises manganese (Mn).

18. The catalyst according to claim 1, wherein said hydrocarbon is selected from the group consisting of butane, pentane, hexane, and heptane.

19. A process for light olefins production from catalytic cracking of hydrocarbon having 4 to 7 carbon atoms, comprising contacting the hydrocarbon having 4 to 7 carbon atoms with a catalyst at the temperature in the range from 400 to 700° C. and the pressure in the range from 0.1 to 10 bars, wherein said catalyst has a core-shell structure comprising zeolite core selected from ferrierite, ZSM-5, or mixture thereof, and silicalite shell having MFI structure, and said catalyst has the following characteristics:

a) the weight ratio of shell to core greater than 0 but less than 4;

b) the mole ratio of silica to alumina ($SiO_2/Al_2O_3$) from 60 to 550;

c) the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.35 to 0.90, and said mesopores comprise pores having pore size from 2 to 5 nm, wherein the proportion of volume of pores having pore size from 2 to 5 nm to the total pore volume is in the range from 0.08 to 0.30.

20. The process for light olefins production according to claim 19, wherein said mesopores comprise pores having pore size from 2 to 5 nm, wherein the proportion of volume of pores having pore size from 2 to 5 nm to the total pore volume is in the range from 0.10 to 0.20.

21. The process for light olefins production according to claim 19, wherein said mesopores further comprise pores having pore size from 5 to 8 nm and pores having pore size from 8 to 18 nm.

22. The process for light olefins production according to claim 19, wherein said zeolite core has the hierarchical pores comprising micropores having pore size in the range of 0.1 to 2 nm, mesopores having pore size in the range of 2 to 50 nm, and macropores having pore size greater than 50 nm, wherein the proportion of volume of mesopores and macropores to the total pore volume is in the range from 0.30 to 0.90.

23. The process for light olefins production according to claim 19, wherein said zeolite core has the hierarchical pores and is arranged in nano-sheet.

24. The process for light olefins production according to claim 19, wherein said silicalite shell has the hierarchical pores and is arranged in nano-sheet.

25. The process for light olefins production according to claim 19, wherein said zeolite core has the mole ratio of silica to alumina in the range from 35 to 320.

26. The process for light olefins production according to claim 25, wherein said catalyst further comprises manganese (Mn) in an amount of from 1 to 15% by weight when comparing with the weight of zeolite core.

27. The process for light olefins production according to claim 19, wherein said zeolite core is the ferrierite having the flower shape-like particle arrangement when analyzed by the scanning electron microscope (SEM) technique at the accelerating voltage of 20 kV with SEI mode.

28. The process for light olefins production according to claim 19, wherein said catalyst has the mole ratio of silica to alumina in the range from 100 to 400.

29. The process for light olefins production according to claim 19, wherein said catalyst comprises the ZSM-5 core having the mole ratio of silica to alumina in the range from 120 to 300 and the silicalite shell, and said catalyst has the weight ratio of shell to core greater than 0 but less than or equal to 1.5.

30. The process for light olefins production according to claim 19, wherein said catalyst comprises the ZSM-5 core having the mole ratio of silica to alumina in the range from 50 to 120 and the silicalite shell, and said catalyst has the weight ratio of shell to core greater than 0 but less than or equal to 3.

31. The process for light olefins production according to claim 19, wherein said catalyst comprises the ferrierite core having the mole ratio of silica to alumina in the range from 150 to 300 and the silicalite shell, and said catalyst has the weight ratio of shell to core greater than 0 but less than or equal to 2.

32. The process for light olefins production according to claim 19, wherein said catalyst comprises the ferrierite core having the mole ratio of silica to alumina in the range from 50 to 150 and the silicalite shell, and said catalyst has the weight ratio of shell to core greater than 0 but less than or equal to 2.

33. The process for light olefins production according to claim 19, wherein said catalyst further comprises manganese (Mn).

34. The process for light olefins production according to claim 19, wherein said zeolite core further comprises manganese (Mn).

35. The process for light olefins production according to claim 19, wherein said zeolite core further comprises manganese (Mn) in an amount of from 1 to 15% by weight when comparing with the weight of zeolite core.

36. The process for light olefins production according to claim 19, wherein the contacting of the hydrocarbon having 4 to 7 carbon atoms with the catalyst is performed at the temperature in the range from 500 to 700° C.

37. The process for light olefins production according to claim 19, wherein said hydrocarbon is selected from the group consisting of butane, pentane, hexane, and heptane.

* * * * *